(12) United States Patent
Matthis et al.

(10) Patent No.: US 8,784,455 B2
(45) Date of Patent: Jul. 22, 2014

(54) BONE ANCHORING DEVICE (71) Applicant: Biedermann Technologies GmbH & Co. KG, Donaueschingen (DE)

(72) Inventors: Wilfried Matthis, Weisweil (DE); Lutz Biedermann, VS-Villingen (DE); Jurgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/708,410

(22) Filed: Dec. 7, 2012

(65) Prior Publication Data
US 2013/0172935 A1 Jul. 4, 2013

Related U.S. Application Data (63) Continuation of application No. 11/960,428, filed on Dec. 19, 2007, now Pat. No. 8,343,191.

(60) Provisional application No. 60/876,670, filed on Dec. 22, 2006.

(30) Foreign Application Priority Data

Dec. 22, 2006 (EP) ..................... 06026705

(51) Int. Cl.
*A61B 17/70* (2006.01)
(52) U.S. Cl.
USPC ........... 606/264; 606/265; 606/266; 606/270; 606/300
(58) Field of Classification Search
USPC .................. 606/264–275, 278, 279, 300–321
See application file for complete search history.

(56) References Cited

U.S. PATENT DOCUMENTS

| 5,037,259 A | 8/1991 | Duran et al. |
| 6,063,090 A | 5/2000 | Schlapfer |

(Continued)

FOREIGN PATENT DOCUMENTS

| CA | 2 346 176 A1 | 4/2000 |
| EP | 1 795 134 A1 | 6/2007 |

(Continued)

OTHER PUBLICATIONS

Notice of Grounds of Rejection issued in parallel Japanese application No. 2007-327360, dated Aug. 22, 2012, 3 sheets.

(Continued)

*Primary Examiner* — Mary Hoffman
*Assistant Examiner* — Christina Negrellirodrigue
(74) *Attorney, Agent, or Firm* — Christie, Parker & Hale, LLP (57) ABSTRACT

A bone anchoring device includes an anchoring element having a shank to be anchored in a bone or a vertebra, a receiving part connected to the shank the receiving part having a first end opposite to the shank and a second end facing the shank, a longitudinal axis passing through the two ends, a bore coaxial with the longitudinal axis extending from the first end through at least a portion of the receiving part and a substantially U-shaped recess for receiving a rod The U-shaped recess forms two free legs extending in the direction of the first end, the legs are provided with an internal thread. A locking device for securing the rod in the receiving part is provided which includes an external thread cooperating with the internal thread. An engagement structure is provided at the circumference of least a part of the outer surface projecting above the first end of the receiving part, the structure being engageable with a tool in a form-fit manner and wherein a maximum outer diameter of said first locking member in the region of said structure is larger than the inner diameter of the internal thread of the receiving part.

13 Claims, 8 Drawing Sheets

(56) References Cited

U.S. PATENT DOCUMENTS

| | | |
|---|---|---|
| 6,224,598 B1 | 5/2001 | Jackson |
| 2003/0100896 A1* | 5/2003 | Biedermann et al. ........... 606/61 |
| 2003/0187434 A1* | 10/2003 | Lin ................................. 606/61 |
| 2006/0036244 A1 | 2/2006 | Spitler et al. |
| 2006/0064091 A1 | 3/2006 | Ludwig et al. |
| 2006/0129149 A1 | 6/2006 | Iott et al. |
| 2006/0149235 A1 | 7/2006 | Jackson |
| 2006/0200129 A1* | 9/2006 | Denti .............................. 606/61 |

FOREIGN PATENT DOCUMENTS

| | | |
|---|---|---|
| FR | 2869215 | 10/2005 |
| JP | 2002-526151 A | 8/2002 |
| JP | 2003-290243 A | 10/2003 |
| JP | 2006-511252 A | 4/2006 |
| TW | 200724081 A | 11/1995 |
| WO | WO 98/25534 | 6/1998 |
| WO | WO 03/041601 A1 | 5/2003 |
| WO | WO 2004/021900 A1 | 3/2004 |
| WO | WO 2006/068711 A2 | 6/2006 |
| WO | WO 2006/089237 A1 | 8/2006 |
| WO | WO 2006/115539 A2 | 11/2006 |
| WO | WO 2006/116437 A2 | 11/2006 |

OTHER PUBLICATIONS

English translation of the Notice of Grounds of Rejection issued in parallel Japanese application No. 2007-327360, dated Aug. 28, 2012, 4 sheets.

European Search Report dated May 30, 2007 for EPO Application No. EP 06026705, European Search Report mailed Jun. 19, 2007, Biedermann Motech GmbH (10 pp.).

* cited by examiner

BONE ANCHORING DEVICE

CROSS-REFERENCE TO RELATED APPLICATION(S)

The present application is a continuation of U.S. patent application Ser. No. 11/960,428, filed on Dec. 19, 2007, which claims the benefit of U.S. Provisional Patent Application Ser. No. 60/876,670, filed Dec. 22, 2006, and claims priority from European Patent Application EP06026705.1, filed Dec. 22, 2006, the entire disclosures of which are incorporated herein by reference.

BACKGROUND

The invention relates to a bone anchoring device comprising a shank to be anchored in a bone or a vertebra and a receiving part connected to the shank for receiving a rod. In particular the invention relates to a polyaxial bone screw wherein the head of the screw and a rod can be fixed independently and which has a reduced size.

U.S. Pat. No. 6,224,598 B1 discloses a threaded plug closure adapted for use in securing a rod member to a bone screw implant, said closure comprising a plug having a threaded cylindrically-shaped outer surface, said plug being received between a pair of arms of a medical implant during use, a central coaxial bore passing entirely through that plug, said central bore having an internal threaded surface which is shaped to receive a set screw. The plug closure and the set screw can be independently installed and the set screw tightened to cooperatively provide capture and locking of the rod in order to secure the rod against translational and rotational movement relative to the bone screw.

US 2003/0100896 A1 discloses a bone anchoring device with a shank and a receiving part connected to it for connecting to a rod. The receiving part has a recess having a U-shaped cross section for receiving the rod forming two open legs. An internal thread is provided on the open legs. A locking assembly is provided comprising a nut member with an external thread which cooperates with the internal thread of the legs and a set screw. The nut member has on one end slits for engagement with a screw tool. The shank has a spherically-shaped head which is pivotably held in the receiving part and a pressure element is provided which exerts pressure on the head when the nut member is tightened. By tightening the set screw the rod is fixed in the receiving part. Hence, the rod and the head can be fixed independently from each other. The internal thread and the cooperating external thread of the nut member are designed as a flat thread. The implant has a compact design, since an outer ring or nut to prevent splaying of the legs is not necessary.

U.S. Pat. No. 6,063,090 discloses a bone anchoring device with a locking assembly consisting of two parts, a tensioning screw fixing the spherical head via an insert without jamming the rod and a tension means fixing the rod.

US 2006/0036244 A1 also discloses a bone anchoring device with a two part locking cap for fixing the head and the rod independently. The tensioning screw has a coaxial recess with a structure for engagement with a tool.

The outer diameter of the locking device is under various aspects determined by the required tightening torque and the thread form. In turn, the overall dimensions of the upper portion of the bone anchoring device are determined by the size of the locking device. For certain applications, it is crucial to have the distance between one bone anchoring device and a neighboring bone anchoring device as small as possible, for example for correcting scoliosis in infants or for the application in the cervical region of the spine.

Based on the foregoing, there is a need for a bone anchoring device with a locking device which has the same reliability as the known devices but which has significantly smaller dimensions of the upper portion in the direction of the rod axis.

SUMMARY OF THE INVENTION

The locking device used in the bone anchoring device according to the invention has a structure for engagement with a tool which is provided at the outer surface in the upper part of the locking device. Hence, the size of the bone anchoring device in the direction of the rod axis can be reduced. The locking device has an improved accessibility for the tool which facilitates the handling during surgery. The bone anchoring device with such a reduced size and improved accessibility is particularly suitable for the application in pediatric surgery or for applications to the cervical spine or other areas where a limited available space requires compact implants. The locking device is designed such that a stop provides safety against disassembly in use.

The rod is locked by means of a locking device having an engagement structure for the engagement with a tool, the engagement structure being provided at the outer circumference of the locking device. The engagement structure projects above the receiving part but does not project beyond the receiving part in a lateral direction.

Additionally, existing polyaxial bone screws which have a single part locking device with the pressure element and the two part locking device can be upgraded according to the invention. Further, the bone anchoring device can be used with the choice of a locking device in two ways. If a single part locking device is selected, it is possible to simultaneously lock the head in the polyaxial position and to fix the rod. If a two part locking device is selected, it is possible to separately lock the head and fix the rod.

Further, the bone anchoring device is compact in size since it is not necessary to use an outer nut or ring to prevent splaying of the legs of the receiving part.

Further features and advantages of the invention will become apparent from the description of embodiments in conjunction with the accompanying drawings.

DETAILED DESCRIPTION OF THE INVENTION

Figure 1:
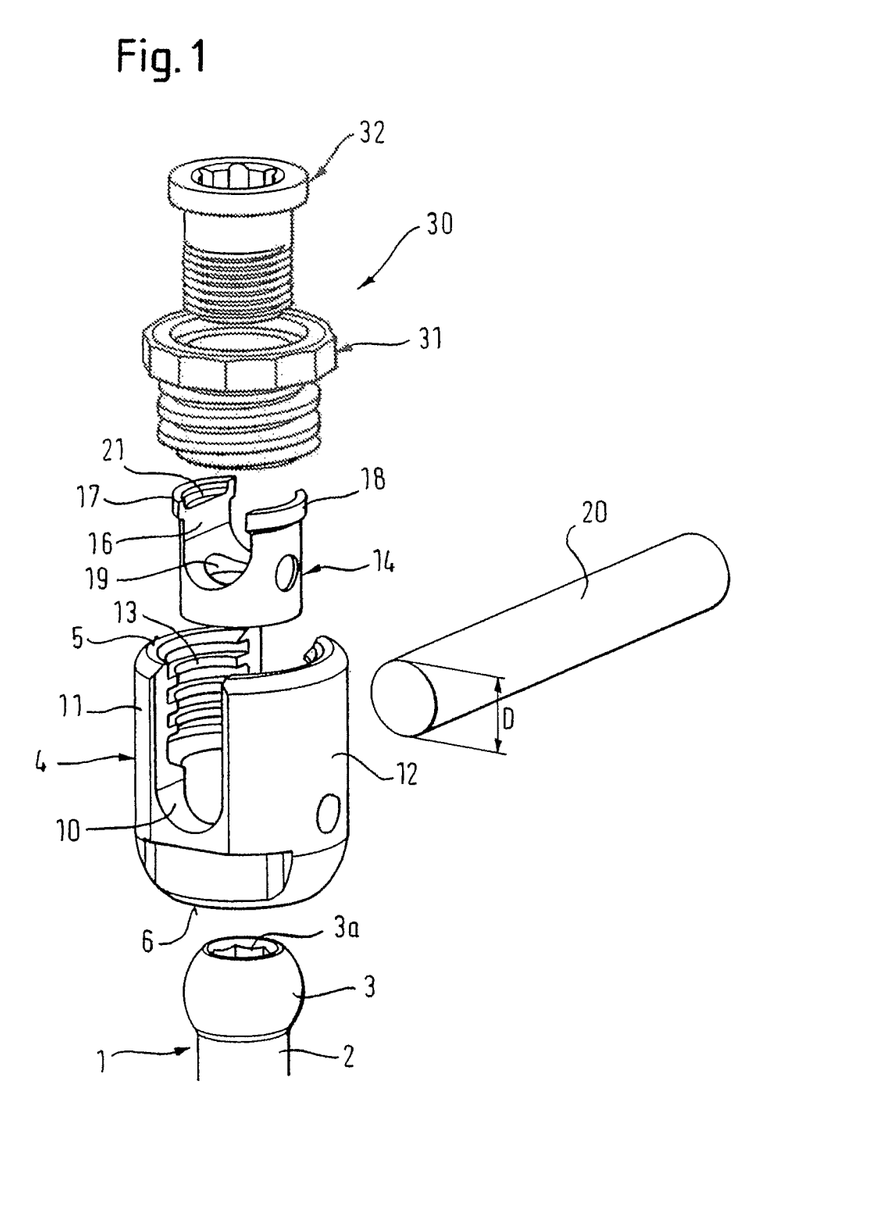
FIG. 1 shows a perspective exploded view of a bone anchoring device according to a first embodiment of the invention.
Figure 2:
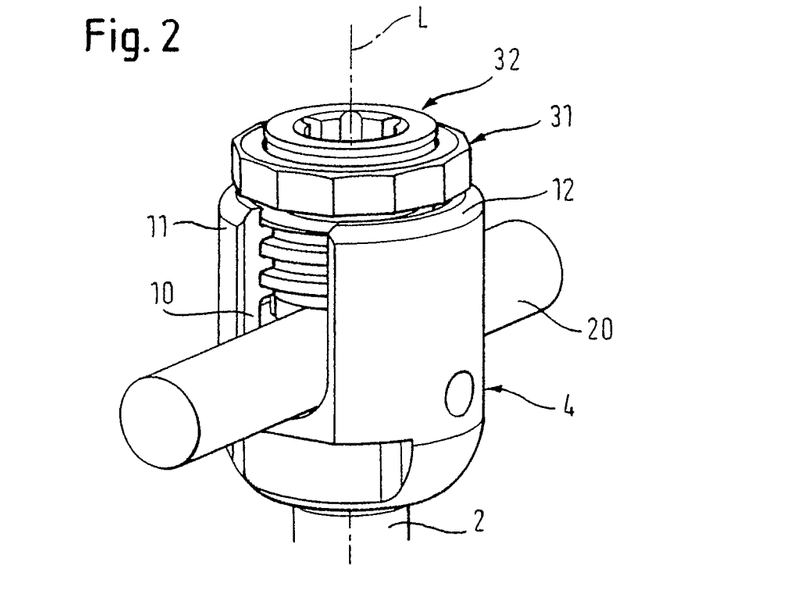
FIG. 2 shows a perspective view of the bone anchoring device in an assembled state.
Figure 3:
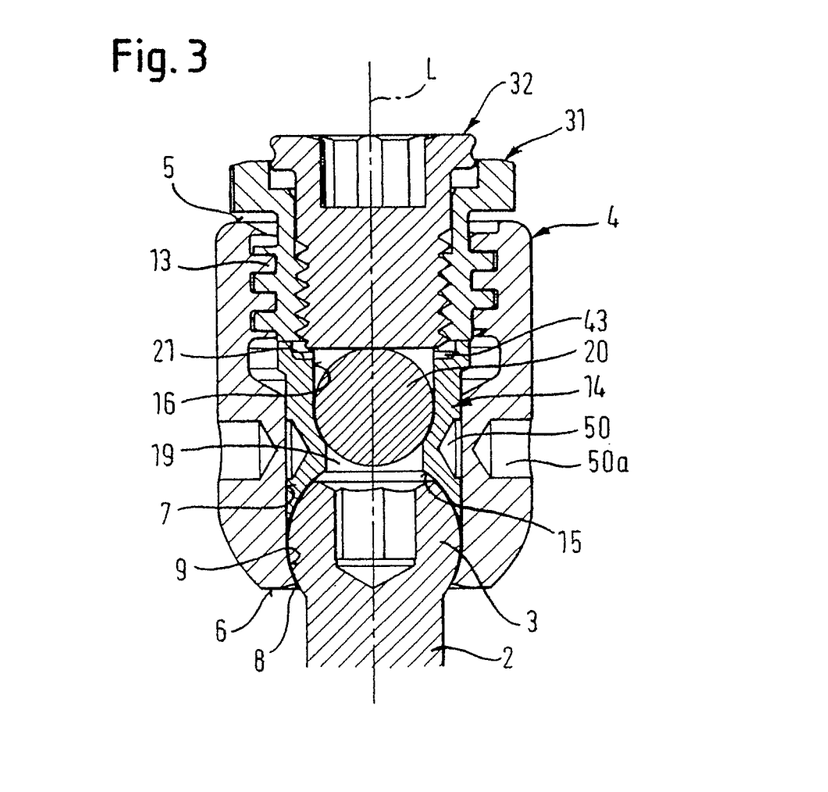
FIG. 3 shows a sectional view of the bone anchoring device in an assembled state the section being taken in a plane perpendicular to the rod axis.
Figure 4:
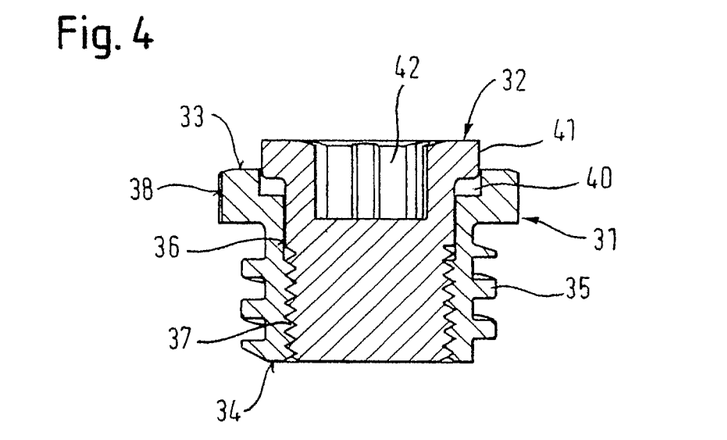
FIG. 4 shows a sectional view of the locking device according to the first embodiment.
Figure 5:
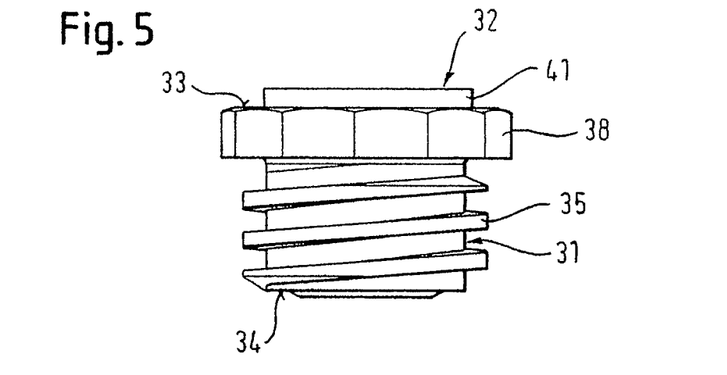
FIG. 5 shows a side view of the locking device of FIG. 4.
Figure 6:
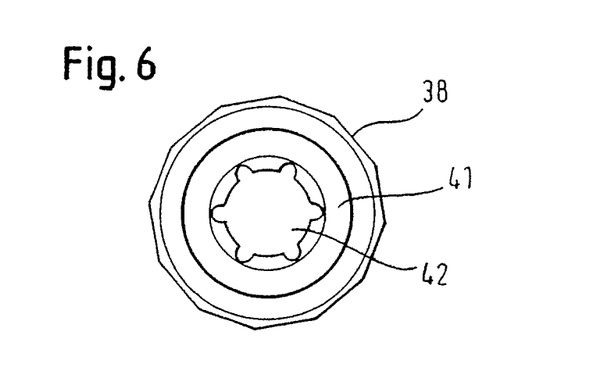
FIG. 6 shows a top view of the locking device according to FIG. 4.
Figure 7:
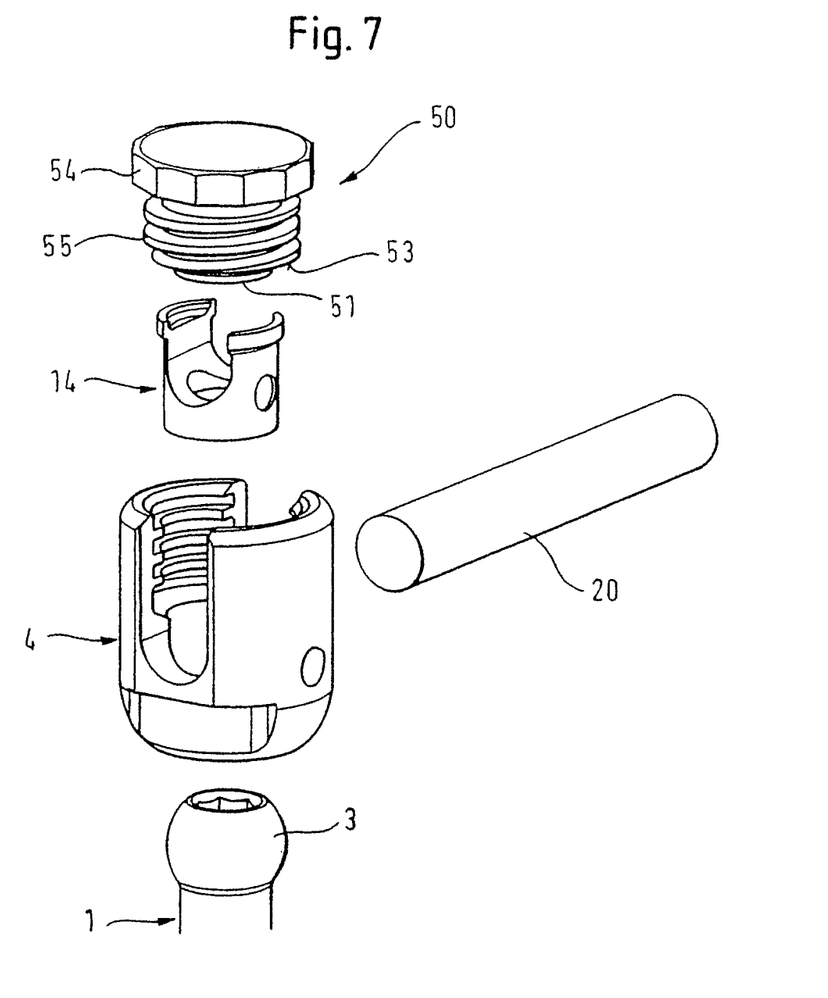
FIG. 7 shows a perspective exploded view of the bone anchoring device according to a second embodiment.

As can be seen in particular in FIGS. 1 to 3, the bone anchoring device according to a first embodiment includes a screw element 1 having a shank 2 with a bone thread (not shown) and a head 3. In the embodiment, the head 3 has the shape of a segment of a sphere. On its surface opposite to the shank, the head 3 comprises a recess 3a for engagement with a tool. The screw element 1 is received in a receiving part 4 which has a first end 5 and a second end 6 and is of approximately cylindrical construction. The two ends are perpendicular to a longitudinal axis L. Coaxially with the longitudinal axis L, a bore 7 is provided which extends from the first end 6 to a predetermined distance from the second end 6. At the second end 6, an opening 8 is provided, the diameter of which is smaller than the diameter of the bore 7. The coaxial bore 7 tapers towards the opening 8. In the embodiment shown it tapers in form of a spherically-shaped section 9. However, the section 9 can have any other shapes such as, for example, a conical shape.

The receiving part 4 further has a U-shaped recess 10 which starts at the first end 5 and extends in the direction of the second end 6 to a distance from the second end 6. By means of the U-shaped recess, two free legs 11, 12 are formed ending towards the first end 5. An internal thread 13 is provided on the inner surface of the legs 11, 12. In the embodiment shown, the internal thread is a flat thread having horizontal upper and lower thread flanks.

Additionally, a pressure element 14 is provided which has a substantially cylindrical construction with an outer diameter sized so as to allow the pressure element 14 to be introduced into the bore 7 of the receiving part and to be moved in the axial direction. On its lower side facing towards the second end 6, the pressure element 14 has a recess 15 cooperating with the head 3. The recess 15 can be spherically-shaped so as to match the contour of the spherical section of the head 3. On its opposite side the pressure element 14 has a U-shaped recess 16 by means of which two free legs 17, 18 are formed. The lateral diameter of this U-shaped recess 16 is selected such that a rod 20 with a diameter D which is to be received in the receiving part 4 can be inserted into the recess 16 and guided laterally therein. The depth of the U-shaped recess 16 is larger than the diameter D of the rod 20 so that the legs 17, 18 extend above the surface of the rod 20 when the rod is inserted. The pressure element further comprises a recess 21 at the inner side of the legs 17, 18 adjacent to the upper end. A bore 19 is provided in the pressure element for accessing the head 3 of the screw element with a tool.

As can be seen in FIG. 3, the pressure element 17 and the receiving part 4 can have crimp bores 50, 50a on opposite sides, respectively, in order to loosely hold the pressure element 14 within a receiving part in a position where the U-shaped recess 16 of the pressure element and the U-shaped recess 10 of the receiving part are aligned.

The bone anchoring device further has a locking device 30. The locking device 30 includes, as shown in particular in FIGS. 1 to 6 a first locking member 31 and a second member 32.

The first locking member 31 has a first end 33 and a second end 34 and a portion with a substantially cylindrical shape with an external thread 35 on the outer surface of that portion. As shown in particular in FIGS. 4 and 5 the external thread 35 is a flat thread which matches the internal thread 13 of the receiving part 4. The first locking member 30 further includes a coaxial bore 36 extending through the entire first locking member. The coaxial bore 36 is provided with an internal thread 37 in at least a portion thereof, the portion corresponding approximately to the outer threaded surface portion of the first locking member. The internal thread 37 is in the embodiment shown formed as a metric thread. The axial length of the threaded outer surface portion with the external thread 35 of the first locking member 31 is such that the external thread 35 cooperates with the internal thread 13 of the legs 11, 12.

The first locking member 31 has adjacent to or in the vicinity of its first end 33 an engagement structure 38 which is provided at the circumference and which can be shaped as a polygon. The outer diameter of the engagement structure 38 in the embodiment shown is larger than the outer diameter of the external thread 35 of the locking member. Hence, the engagement structure 38 can form a stop when the first locking member is tightened. On the other hand, the maximum outer diameter of the engagement structure 38 is equal to or smaller than the outer diameter of the receiving part measured between opposite sides of the legs, as can particularly be seen in FIGS. 2 and 3. Hence, the engagement structure 38 does not laterally project beyond the outer contour of the receiving part 4. The minimum outer diameter is larger than the inner diameter of the internal thread 13. The engagement structure 38 serves for engagement with a tool in a form-fit manner. It needs not to be in the shape of a polygon, but can have other shapes. For example, the outer contour of the engagement structure can be triangular, square, star-shaped, circular with two opposite flattened sides, or otherwise shaped.

Adjacent to its first end 33 the first locking member 31 comprises a recess 40 which serves for accommodating a part of the second locking member described below. The total length of the first locking member 31 in the axial direction is such that, as shown in FIG. 3, in an assembled state the first locking member 31 presses with its second end 34 on to the legs 17, 18 of the pressure element 14 which in turn presses onto the head 3.

The second locking member 32 is a screw which is to be screwed into the coaxial bore 36 of the first locking member 31. On one side the second locking member 32 has a thread free section with an annular shoulder 41, the outer diameter of which is slightly smaller than the inner diameter of the recess 40 of the first locking member, so that the shoulder 41 can be accommodated in the recess 40. Hence, the recess 40 forms a stop for screwing-in the second locking member 32. Additionally, the second locking member 32 comprises a recess 42 at the end where the annular shoulder 41 is provided for engagement with a tool. The recess 42 can be shaped as a hexagon recess or can have axial grooves arranged in a shape of a star.

The axial length of the second locking member 32 is such that when the second locking member 32 is inserted into the first locking member and the locking device is screwed-in between the legs of the receiving part, the second locking member presses onto the rod 20, but does not contact the pressure element 14. As can be seen in FIG. 3, there is a gap 43 between the bottom of the recess 20 of the pressure element and the lower side of the second locking member.

The shoulder 41 can serve for gripping the second locking member in order to assemble it with the first locking member and to provide a stop.

In operation, first, at least two usually preassembled bone anchoring devices each having a screw element 1, the receiving part 4 and the pressure element 14 are screwed into the bone.

Thereafter, the rod 20 is inserted into the U-shaped recess 10 of the receiving part 4. Then the locking device 30 comprising the first locking element 31 and the second locking element 32 which can be preassembled, is screwed-in between the legs 11, 12 of the receiving part 4. The first locking element 31 is then tightened by applying a tool (not shown) to the engagement structure 38 until the first locking member 31 presses onto the free legs of the pressure element. By tightening the first locking member 31 the pressure element 14 exerts a pressure onto the head 3 of the screw element 1 to lock the head 3 in its angular position within the receiving part 4. The stop provided by the engagement structure 38 limits the applied force to a specific value.

When the head is locked, the rod 20 is still slidable in the receiving part. By tightening the second locking member 32 the second locking member 32 moves downwards and presses onto the rod to fix the rod in its position. The force exerted onto the rod can be well defined using the stop provided by the annular shoulder 41 abutting against the bottom of recess 40.

By means of providing the engagement structure 38 on the outer circumference of the first locking member the first locking member can be made smaller in its dimensions, in particular, with a smaller diameter of the outer threaded surface section. If the first locking member 31 can be made with a smaller outer diameter, in turn, the receiving part can be made with a smaller outer diameter. As a result thereof, the distance between two bone anchoring devices in the direction of the rod can be made smaller. The shoulder 41 facilitates handling of the second locking member.

A second embodiment of the bone anchoring device is shown in FIGS. 7 to 9a and 9b. Parts which are identical to the first embodiment are designated with the same reference numerals and the description thereof will not be repeated. The bone anchoring device according to the second embodiment comprises a single part locking device 50.

Figure 8:
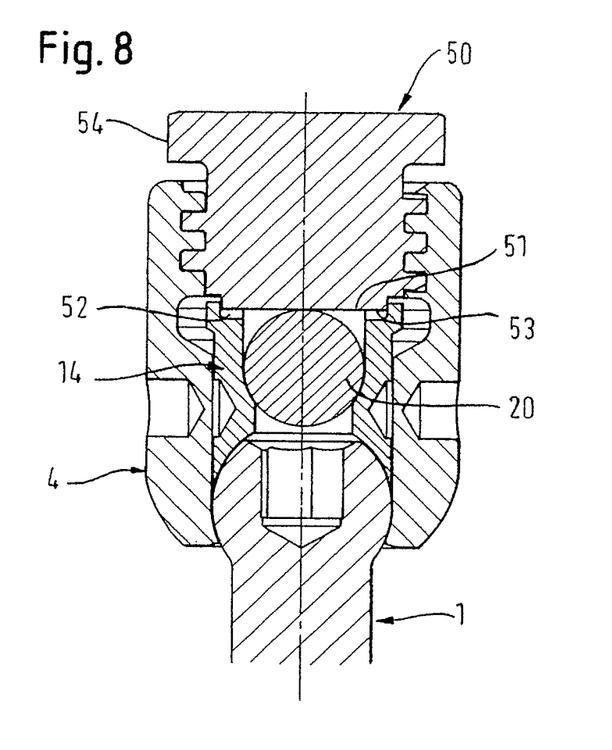
FIG. 8 shows a sectional view of the bone anchoring device according to the second embodiment in an assembled state, the section being taken in a plane perpendicular to the rod axis.
Figure 9A:
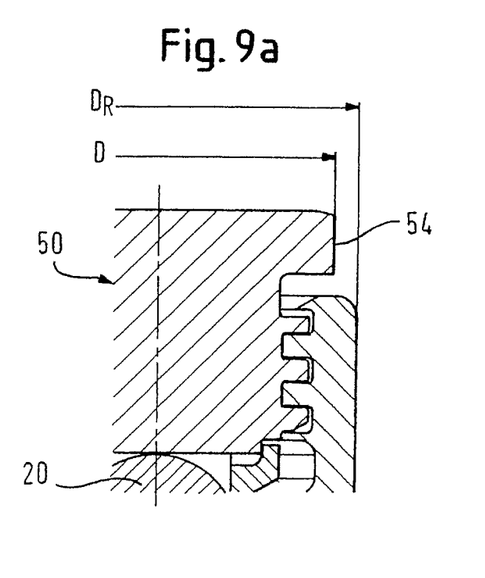
FIG. 9a shows an enlarged portion of FIG. 8.
Figure 9B:
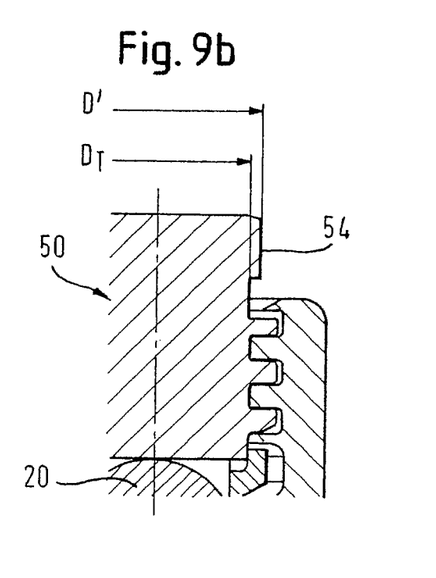
FIG. 9b shows the portion as depicted in FIG. 9a with a locking element having a minimized outer diameter of the engagement structure.

As shown in FIGS. 7 to 9b the single part locking device is an inner screw which can be screwed between the legs 11, 12 of the receiving part 4. In this embodiment, the thread 55 of the screw is a flat thread cooperating with the flat thread provided at the legs. On its side facing the pressure element 14 the inner screw has a projection 51, the diameter of which is sized so that the projection 51 can press onto the rod 20 without touching the pressure element. The length of the single part locking device 50 and the length of the cylindrical projection 51 is such that as shown in FIG. 8, in the tightened state, the cylindrical projection 51 contacts the rod and there is a gap 52 between the lower surface 53 of the single part locking device and the legs 17, 18 of the pressure element 14. On the side opposite to the projection 51 the single part locking device 50 has an engagement structure 54, which can have a polygon shape for engagement with a tool. The engagement structure 54 is similar to the engagement structure 38 of the first locking element 31 of the two-part locking device 30 of the first embodiment. As shown in FIG. 9a, the outer diameter $D_o$ is smaller than the outer diameter $D_R$ of the receiving part 4 in the region of the legs. As shown in FIG. 9b, in an even smaller version of the locking element, the outer diameter $D'_o$ is only slightly larger than the inner diameter of the inner thread $D_T$.

The engagement structure projects above the receiving part 4. Therefore the tightening of the locking element with a tool during surgery is facilitated since the engagement structure is easily accessible with the tool.

Use of the bone anchoring device is the same as for the first embodiment with the exception that the single part locking device 50 is used instead of the locking device 30 of the first embodiment. In this case, the single part locking device 50 presses onto the rod which in turn presses onto the pressure element 14 to fix the head 3 in the receiving part 4. Hence, the rod and the head are fixed simultaneously.

Figure 10:
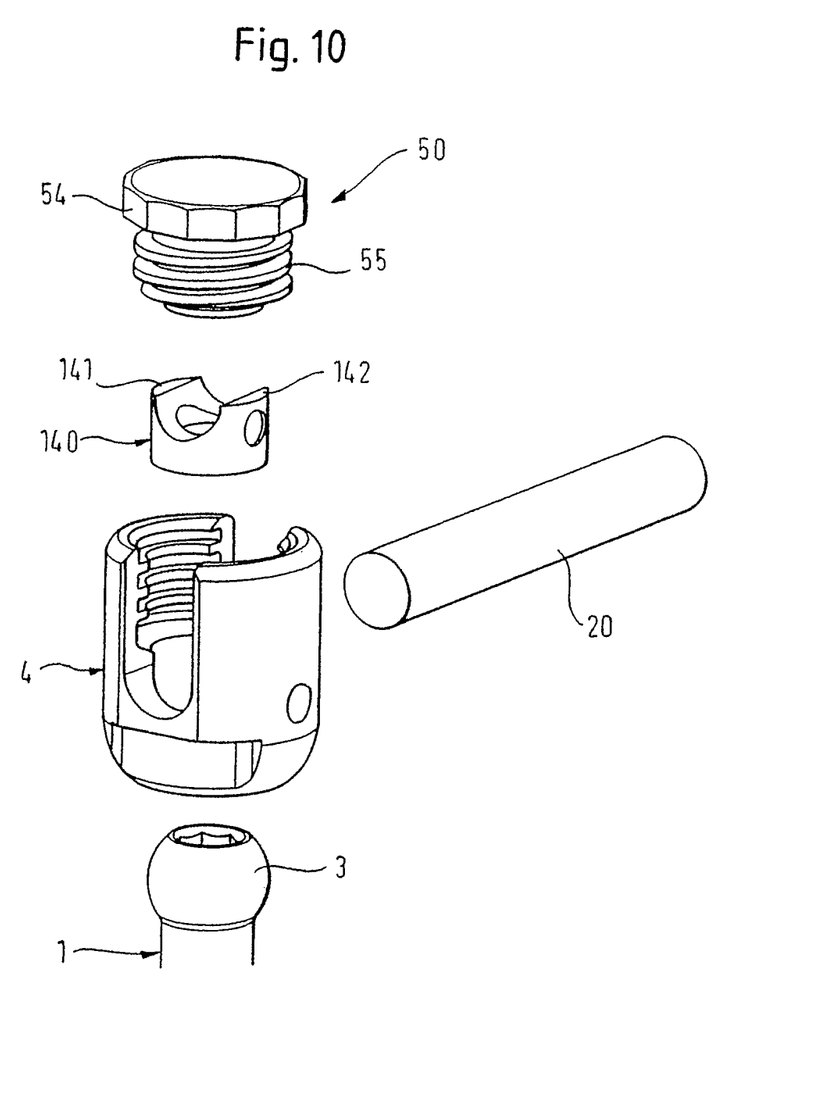
FIG. 10 shows a perspective exploded view of the bone anchoring device according to a third embodiment.

FIG. 10 shows a third embodiment of the bone anchoring device. It differs from the second embodiment mainly by the shape of the pressure element. All other parts are the same. The pressure element 140 differs from the pressure element 14 of the first and second embodiment in that it has short legs 141, 142, which do not project above the rod when the rod is inserted. All other features are the same as that of the pressure element 14.

In a further modification, the pressure element 140 does not have a recess for receiving the rod and also no legs. It can be formed as a pressure disk. In a further modification the single part locking element 30 does not have a projection 51 for pressing onto the rod.

Figure 11:
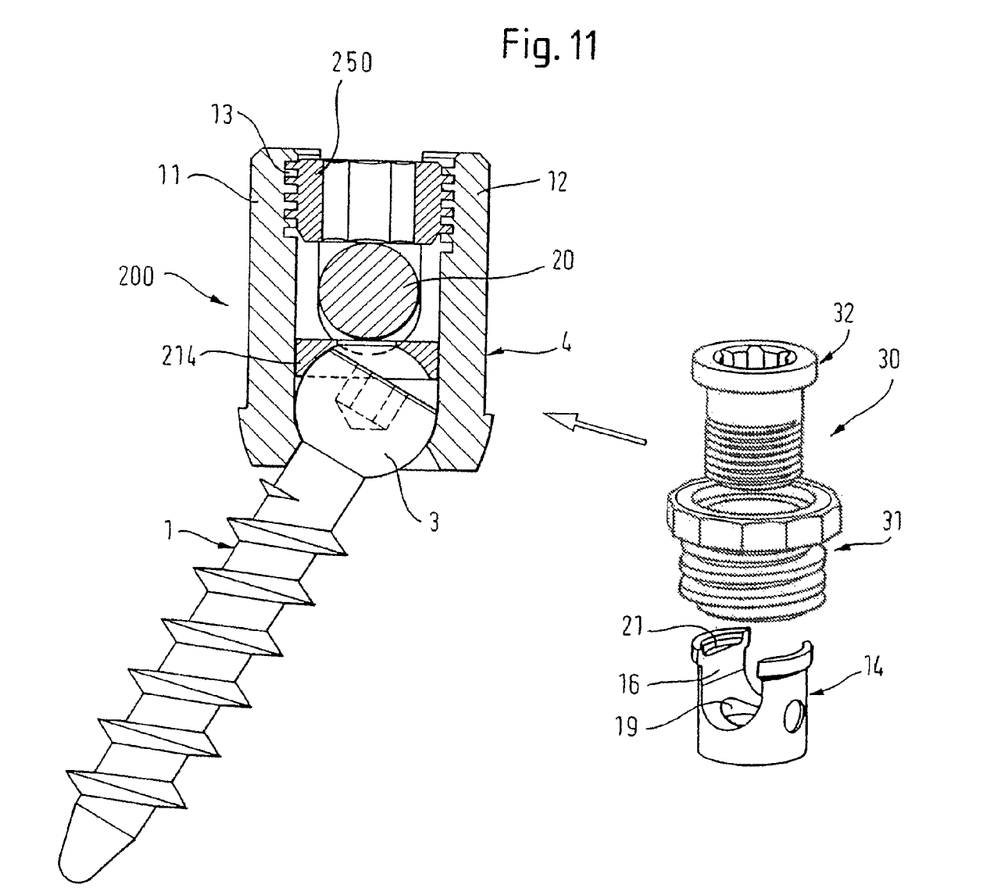
FIG. 11 schematically shows the locking device and the pressure device of the bone anchoring device according to the first embodiment to be used as an upgrade of an existing polyaxial bone screw.

FIG. 11 schematically shows the locking device 30 and the pressure element 14 of the bone anchoring device according to the first embodiment to be used as an upgrade of an existing polyaxial bone screw with a single part locking element. A known polyaxial bone screw 200 has a single part locking element 250 in form of a set screw and a pressure disk 214. Known anchoring devices with a two-part locking device (not shown) would have a larger size in terms of the outer diameter of the receiving part compared to the bone anchoring device having the single part locking element 250. It is, however, possible to upgrade the existing bone anchoring device 200 by exchanging the set screw 250 and the pressure disk 214 with the locking device 30 and the pressure element 14 according to the first embodiment. Hence, a bone anchoring device with minimized dimensions and with the advantage of being able to fix the rod and the head independently is provided.

Figure 12:
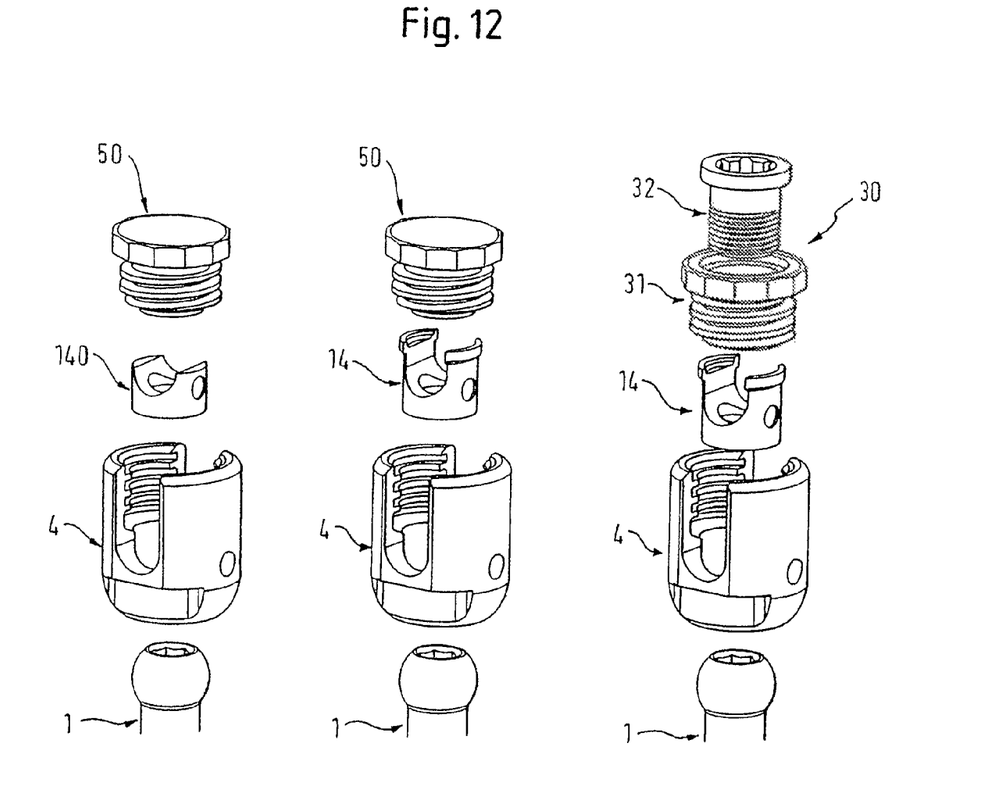
FIG. 12 shows a modular system of bone anchoring devices including the bone anchoring devices of the first, second and third embodiments.

FIG. 12 shows a modular system of bone anchoring devices including the bone anchoring devices of the first, second and third embodiments. The single-part and the two-part locking devices can be used interchangeably if the pressure element 14 is used. Alternatively, the single-part locking device can be used with the pressure element 14 or 140.

A surgeon can select whether the single part locking device 50 or the two-part locking device 30 is to be used in conjunction with the same bone anchoring device. For certain applications a single part locking device for simultaneous locking of head and rod may be advantageous, in particular, if the fixation has to take place rapidly. For certain other applications it may be advantageous to have the separate fixation of the head and the rod. Since the surgeon can use the same bone anchoring device and is free to select a desired locking device, it is not necessary to have different receiving parts with different pressure elements for different bone anchoring devices available.

Modifications of the embodiments are possible. Instead of a flat thread other thread forms can be used. Further, the section 10 of the receiving part 4 against which the head 3 rests needs not to be spherically-shaped but can have any other shape as long as the head 3 is held by the edge of the opening 8 like a ball and socket joined. In a further modification, the receiving part is designed so as to allow the introduction of the head from the bottom of the receiving part from the second end.

What is claimed is:

1. A bone anchoring device comprising:
   an anchoring element comprising a shank to be anchored in a bone or a vertebra;
   a receiving part connectable to the shank, the receiving part comprising:
      a first end opposite to the shank and a second end facing the shank, when connected to the shank;
      a longitudinal axis passing through the two ends;
      an outer surface at the first end, a side surface extending between the two ends, and an edge region between and inclined relative to the outer surface and the side surface;
      a bore coaxial with the longitudinal axis extending from the first end through at least a portion of the receiving part; and
      a substantially U-shaped recess for receiving a rod, the recess forming two free legs extending in the direction of the first end, the legs being provided with an internal thread and each including respective portions of the outer surface, the side surface, and the edge region; and
   a locking device for securing the rod in the receiving part, said locking device comprising;
      a first locking member having a first end and a second end, the first locking member being provided with an external thread on at least a portion thereof which cooperates with the internal thread provided on said legs to connect the first locking member to the receiving part, a coaxial bore passing entirely through the first locking member and an internal thread provided in at least a portion of said bore;
      a second locking member, the second locking member having an outer surface with an external thread in at least a portion thereof which cooperates with the internal thread provided at said bore of the first locking member; and
      a non-cylindrical engagement structure provided at a perimeter of at least a part of an outer surface of the first locking member projecting above the first end of the receiving part when connected to the receiving part, the structure being engageable with a tool in a form-fit manner, and wherein said engagement structure is larger than the inner diameter of the internal thread of the receiving part and is equal to or smaller than an inner dimension of the edge region of the receiving part.

2. The bone anchoring device of claim 1, wherein said anchoring element comprises a head and wherein said receiving part comprises a region adjacent to said second end for pivotably receiving said head.

3. The bone anchoring device of claim 2, further comprising a pressure element arranged in the receiving part between the head and the locking device for exerting pressure onto said head to lock the head in the receiving part.

4. The bone anchoring device of claim 3, wherein said pressure element has a substantially U-shaped recess for receiving at least a part of the rod, the depth of the recess being larger than the diameter of the rod.

5. The bone anchoring device of claim 1, wherein said first locking member is designed so as to lock the head without fixing the rod and wherein said second locking member is designed so as to fix rod.

6. The bone anchoring device of claim 1, wherein the outer contour of said engagement structure is a polygon or a star.

7. The bone anchoring device of claim 1, wherein the outer diameter of said engagement structure is larger than the outer diameter of the external thread of the locking device.

8. A modular bone anchoring system comprising:
   an anchoring element comprising a shank to be anchored in a bone or a vertebra;
   a receiving part connectable to the shank the receiving part comprising a first end opposite to the shank and a second end facing the shank when connected to the shank, a longitudinal axis passing through the two ends, an outer surface at the first end, a side surface extending between the two ends, an edge region between and inclined relative to the outer surface and the side surface, a bore coaxial with the longitudinal axis extending from the first end through at least a portion of the receiving part, and a substantially U-shaped recess for receiving a rod, the recess forming two free legs extending in the direction of the first end, the legs being provided with an internal thread and each includinci resoecti veportions of the outer surface, the side surface, and the edge region;
   a pressure element arrangeable in the receiving part between the head and the locking device for exerting pressure onto said head to lock the head in the receiving part, wherein said pressure element has a substantially U-shaped recess for receiving at least a part of the rod, the depth of the recess being, larger than the diameter of the rod;
   a two-part locking device for securing the rod in the receiving part, said two-part locking device comprising an engagement structure provided at a perimeter of at least a part of an outer surface of the two-part locking device and configured to project above the first end of the receiving part when connected to the receiving part, the structure being engageable with a tool in a form-fit manner, and wherein said engagement structure is larger than the inner diameter of the internal thread of the receiving part and is smaller than an inner dimension of the edge region of the receiving part; and
   a single-part locking device for securing the rod in the receiving part, said single-part locking device comprising an engagement structure provided at a perimeter of at least a part of an outer surface of the single-part locking device and configured to project above the first end of the receiving part when connected to the receiving part, wherein said engagement structure is larger than the inner diameter of the internal thread of the receiving part and is equal to or smaller than an inner dimension of the edge region of the receiving part.

9. The modular system of claim 8, wherein the two-part locking device and the single-part locking device can be used interchangeably.

10. The modular bone anchoring device of claim 8, wherein the outer contour of said engagement structure of at least one of the two-part locking device and the single-part locking device is a polygon or a star.

11. The modular bone anchoring device of claim 8, wherein the outer diameter of said engagement structure of the two-part locking device and the single-part locking device is larger than the outer diameter of the external thread of the locking device.

12. A method of attaching a bone anchoring device to a bone, the bone anchoring device comprising an anchoring element having a shank to be anchored in a bone or a vertebra, a receiving part connectable to the shank, the receiving part comprising a first end opposite to the shank and a second end facing the shank when connected to the shank, a longitudinal axis passing through the two ends, an outer surface at the first end, a side surface extending between the two ends, an edge region between and inclined relative to the outer surface and the side surface, a bore coaxial with the longitudinal axis extending from the first end through at least a portion of the receiving part, and a substantially U-shaped recess for receiving a rod, the recess forming two free legs extending in the direction of the first end, the legs being provided with an internal thread and each including respective portions of the outer surface, the side surface, and the edge region, the bone anchoring device further comprising a locking device for securing the rod in the receiving part, said locking device comprising a first locking member having a first end and a second end, the first locking member being provided with an external thread on at least a portion thereof which cooperates with the internal thread provided on said legs to connect the first locking member to the receivingpart, a coaxial bore passing entirely through the first locking member, and an internal thread provided in at least a portion of said bore, a second locking member, the second locking member having an outer surface with an external thread in at least a portion thereof which cooperates with the internal thread provided at said bore of the first locking member, and an engagement structure provided at a perimeter of at least a part of an outer surface of the first locking member projecting above the first end of the receiving part when connected to the receiving part, the structure being engageable with a tool in a form-fit manner, and wherein said engagement structure is larger than the inner diameter of the internal thread of the receiving part and is equal to or smaller than an inner dimension of the receiving part, the method comprising:

anchoring the shank into a bone;

inserting a rod in the U-shaped recess of the receiving part;

fixing the shank of the anchoring element relative to the receiving part, the fixing comprising screwing the first locking member to the internal threads of the free legs, and tightening the first locking member by the tool engaging the engagement structure provided at the perimeter of the at least a part of the outer surface of the first locking member;

fixing the rod in the U-shaped recess of the receiving part by screwing the second locking member to the internal thread of the first locking member and tightening the second locking member over the rod.

13. A bone anchoring device comprising:

an anchoring element comprising a shank to be anchored in a bone or a vertebra;

a receiving part connectable to the shank, the receiving part comprising:

a first end opposite to the shank and a second end facing the shank, when connected to the shank;

a longitudinal axis passing through the two ends:

a bore coaxial with the longitudinal axis extending from the first end through at least a portion of the receiving part; and    a substantially U-shaped recess for receiving a rod, the recess forming two free legs extending in the direction of the first end, the legs being provided with an internal thread; and a locking device for securing the rod in the receiving part, said locking device comprising:

a first locking member having a first end and a second end, the first locking member being provided with an external thread on at least a portion thereof which cooperates with the internal thread provided on said legs to connect the first locking member to the receiving part, a coaxial bore passing entirely through the first locking member, and an internal thread provided in at least a portion of said bore;

a second locking member, the second locking member having an outer surface with an external thread in at least a portion thereof which cooperates with the internal thread provided at said bore of the first locking member; and    an engagement structure provided at a perimeter of at least a part of an outer surface of the first locking member projecting above the first end of the receiving part when connected to the receiving part, the structure being engageable with a tool, and wherein the engagement structure is larger than the inner diameter of the internal thread of the receiving part, wherein the first locking member has a recess adjacent to the first end, and the second locking member includes a shoulder, wherein the shoulder is larger than the outer diameter of the external thread of the second locking member, and wherein the shoulder is smaller than an inner perimeter of the recess of the first locking member, such that the shoulder can be accommodated in the recess.

\* \* \* \* \*

UNITED STATES PATENT AND TRADEMARK OFFICE
CERTIFICATE OF CORRECTION

PATENT NO.       : 8,784,455 B2
APPLICATION NO.  : 13/708410
DATED            : July 22, 2014
INVENTOR(S)      : Matthis et al.

Page 1 of 1

It is certified that error appears in the above-identified patent and that said Letters Patent is hereby corrected as shown below:

On the Title Page

| | |
|---|---|
| Item [57], line 8 | Delete "rod" |
| | Insert -- rod. -- |
| Item [57], line 10 | Delete "end, the" |
| | Insert -- end. The -- |

In the Specification

| | |
|---|---|
| Column 3, line 62 | Delete "17" |
| | Insert -- 14 -- |

In the Claims

| | |
|---|---|
| Column 8, Claim 8, line 21 | Delete "includinci resoecti veportions" |
| | Insert -- including respective portions -- |
| Column 9, Claim 12, line 19 | Delete "receivingpart," |
| | Insert -- receiving part, -- |
| Column 9, Claim 12, line 32 | After "dimension" |
| | Insert -- of the edge region -- |

Signed and Sealed this
Fourteenth Day of October, 2014

Michelle K. Lee
*Deputy Director of the United States Patent and Trademark Office*